United States Patent [19]

Cosentino et al.

[11] Patent Number: 5,279,735
[45] Date of Patent: Jan. 18, 1994

[54] STERILANT SOLUTIONS FOR HOLLOW FIBER MEMBRANES

[75] Inventors: Louis C. Cosentino, Plymouth; Robert T. Hall, Welch; Rosario M. Marino, Minnetonka; Igor P. Zdorov, Plymouth, all of Minn.

[73] Assignee: Minntech Corporation, Minneapolis, Minn.

[21] Appl. No.: 736,017

[22] Filed: Jul. 25, 1991

[51] Int. Cl.$^5$ ............................................. B01D 63/02
[52] U.S. Cl. ........................... 210/321.69; 210/321.78; 210/500.23
[58] Field of Search ................... 210/321.69, 636, 138, 210/141, 143, 746, 764, 765, 321.78, 500.23; 514/23, 25

[56] References Cited

U.S. PATENT DOCUMENTS 4,695,385 9/1987 Boag ............................. 210/143 X
4,900,721 2/1990 Bansemir et al. ................. 514/23 X Primary Examiner—Frank Spear
Attorney, Agent, or Firm—Barbara A. Wrigley

[57] ABSTRACT

An oxidizing sterilant solution comprising percarboxylic acid is disclosed which contains a colorant that is color stable for a useful period in the oxidizing, sanitizing environment.

28 Claims, No Drawings

STERILANT SOLUTIONS FOR HOLLOW FIBER MEMBRANES

FIELD OF THE INVENTION

The invention relates to colored aqueous oxidant sterilizing compositions. In particular, the aqueous oxidant sterilizer compositions can be used in many environments to reduce or eliminate bacterial population.

BACKGROUND OF THE INVENTION

A variety of sterilants have been proposed for use in the aqueous solutions used to disinfect and sanitize a variety of surfaces. The selection of the sterilants is limited by the toxicity of many antimicrobial compositions. Percarboxylic acids are often used as antimicrobial compositions. One preferred antimicrobial composition is peracetic acid which is manufactured by contacting a source of acetic acid, typically acetic acid or acetic anhydride, with hydrogen peroxide resulting, through an equilibrium reaction, in the production of peracetic acid in significant proportion. Percarboxylic acids are believed to associate with the lipid membrane of a variety of cell walls in microorganisms to result in lysis and death of the contaminating growth of the undesirable microorganisms. Percarboxylic acid solutions provide a strongly oxidizing sanitizing environment.

Clinical personnel have found the use of percarboxylic acid solutions difficult because the colorless material cannot be easily identified once removed from its container. Further, after a dilution has been made, the diluted material can not be easily differentiated from the concentrate. Accordingly, there has been a substantial need in this art for some means to determine the nature of the material.

BRIEF DISCUSSION OF THE INVENTION

We have found in our experiments that a color-stable dye can be used to color a percarboxylic acid solution. A concentration of dye can be used such that the concentrate selected by the user can have a distinctive depth of color while its dilution product or use solution that is used within the sanitizing regiment can have its own lighter, but distinctive color depth. In this way, the percarboxylic acid concentrate and use solutions can be distinguished and can be distinguished from other solutions used. Further, the presence of percarboxylic acid solutions in and around glassware, process apparatus and other equipment can easily be determined by inspecting the color of the solution. In addition, we have found that the colorants that we have found which are stable in the highly oxidizing percarboxylic acid sanitizers, do not stain the surfaces or equipment that contacts the sterilant material. Lastly, the combination of dye and percarboxylic acid solutions effectively sanitize and preserve synthetic membranes without causing significant degradation of their polymeric materials. By color stable we mean the dye or colorant retains color for a period useful in the application of the percarboxylic acid. The period of time may be as short as one minute, five minutes, or as long as a few days, a year or longer.

DETAILED DISCUSSION

We have found that the safety and utility of percarboxylic acid sanitizing solutions can be improved by incorporating into the solution produced by reacting a source of carboxylic acid and a source of peroxide, a dye which is color stable in the sanitizing oxidizing environment for at least about one minute. In addition to being color stable in the percarboxylic acid environment, the dye preferably does not stain the surfaces or equipment that contacts the sterilant material.

We have found many useful dyes. Useful dyes are freely soluble in aqueous percarboxylic acids, are strongly colored at low concentration and are stable in the solution for a useful period. The dye is also preferably nontoxic and safe to use, more preferably is it FDA approved.

Useful dyes are generally conjugated aromatics and/or heterocyclics and may have the following formulas:

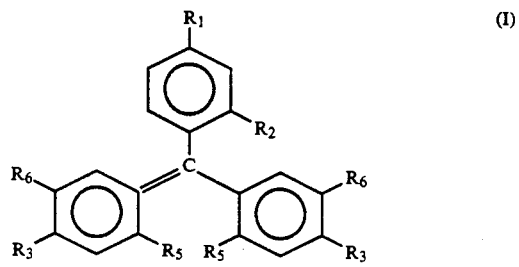
(I)

wherein $R_1$ and $R_2$ independently represent —H or —$SO_3M$ wherein M represents H+ or an alkali metal or alkaline earth metal salt; each $R_3$ independently represents —H, —$N(R_4)_2$, or =$N^+(R_4)_2$; $R_4$ represents —H or $C_{1-4}$ alkyl; each $R_5$ independently represents —H or —$SO_3M$ wherein M represents H+ or an alkali metal or alkaline earth metal salt, or $R_5$ together represent —O—; $R_6$ independently represents —H or $C_{1-4}$ alkyl;

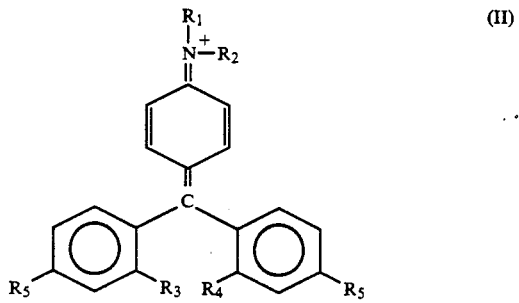
(II)

wherein $R_1$ represents —H or $C_{1-4}$ alkyl; $R_2$ represents —H, phenyl or $C_{1-4}$ benzyl; $R_3$ and $R_4$ independently represent —H, —$SO_3M$ wherein M represents H+ or an alkali metal or alkaline earth metal salt; and $R_5$ independently represents —H, or —$N(R_6)R_7$ wherein $R_6$ represents —H, $C_{1-4}$ alkyl, and $R_7$ represents —H, $C_{1-4}$ alkyl benzene or —$SO_3M$ substituted $C_{1-4}$ alkyl benzene; and $$Ar-N=N-Br \qquad (III)$$

wherein Ar and Br are independently

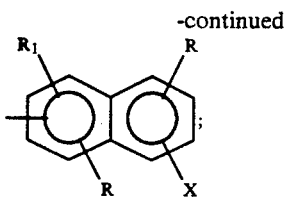

or

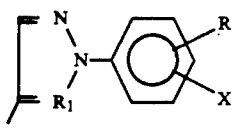

wherein each X represents —H or —SO$_3$M wherein M represents H$^+$ or an alkali metal or alkaline earth metal salt; R independently represents —H, C$_{1-12}$ alkyl, a phenyl, a C$_{1-12}$ substituted phenyl, a —NH-C$_{1-12}$ alkyl, a —NH—phenyl, a —NH-C$_{1-12}$ alkyl substituted phenyl, wherein at least one X is not H$^+$ and at least one R is not —H; R$_1$ represents —H or —OH; and wherein the color of the azo dye is stable for a useful period of time in the sanitizing oxidizing environment.

We have found that these dyes are generally stable in the oxidizing sanitizing environment of the percarboxylic acid solutions, provide at low concentrations (1 to 0.001 wt-%) significant visual indication of the identity of the solutions, and do not interact with a hollow fiber membrane to stain the membrane.

Specific, non-limiting examples of useful dyes include 4-(2-methyl-1-naphthylazo)-1-(3-methyl)benzene sulfonic acid sodium salt, 4-(2-phenyl amino-1-naphthylazo)-1-benzene sulfonic acid sodium salt, 3-(4-sodium sulfoxylnaphthylazo) (2-phenyl) benzene sulfonic acid sodium salt, 3-[[4-(phenylamino)phenyl]azo]-benzenesulfonic acid sodium salt, 4-(2-dodecyl phenyl-1-naphthylazo)benzenesulfonic acid sodium salt, 1-azo phenyl-2-phenyl amino-6,8-naphthalene disulfonic acid sodium salt, N-Ethyl-N-[4-[[4-]ethyl[(3-sulfophenyl)methyl]amino]phenyl](2-sulfophenyl)methylene]-2,5-cyclohexadien-1-ylidene]-3-sulfobenzenemethanaminium hydroxide inner salt, disodium salt, erioglaucine, sulforhodamine, 4,5-dihydro-5-oxo-1-(4-sulfophenyl)-4-[(4-sulfophenyl)azo]-1H-pyrazole-3-carboxylic acid trisodium salt, azo rubin, and others. We have found that these dyes have no easily oxidizable functional groups, are based on substituted aromatic nuclei which provide a strong color and are generally FDA approved.

Preferably, the dye is of the class of azo dyes represented by (III), and more preferably, the dye is of the class of azo dyes represented by (III) wherein Ar and Br are independently

or

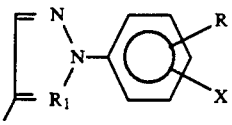

wherein each X represents —H or —SO$_3$M wherein M represents H$^+$ or an alkali metal or alkaline earth metal salt; R independently represents —H, C$_{1-12}$ alkyl, a phenyl, a C$_{1-12}$ substituted phenyl, a —NH-C$_{1-12}$ alkyl, a —NH—phenyl, a —NH—C$_{1-12}$ alkyl substituted phenyl, wherein at least one X is not H$^+$ and at least one R is not —H; R$_1$ represents —H or —OH; and wherein the color of the azo dye is stable for a useful period of time in the sanitizing oxidizing environment.

We have found that the visually detectible oxidizing sterilants of this invention can be manufactured by forming stable peroxy containing concentrates based on aliphatic monopercarboxylic acids. The concentrates of the invention are characterized by a content of 0.1% to 50 wt-% of a peracid or a corresponding aliphatic carboxylic acid, 0.1-50% by weight of hydrogen peroxide, as well as an effective amount of the colorant of the invention. More particularly, the invention relates to a stable peroxy containing concentrate useful for the production of anti-microbial agents comprising from 0.5 to 20 wt-% of a peracetic acid; from about 0.1 to 40 wt-% of a hydrogen peroxide, and most preferably, the stable concentrates of the invention can contain 0.1-50 wt-% of the peracetic acid component, and a sufficient amount of hydrogen peroxide to maintain the concentration of peracetic acid in the aqueous solution. In addition to the source of acetic acid and peroxide in the solution, the solutions can contain stabilizers useful for maintaining an effective concentration of peroxy compound (either the hydrogen peroxide or the peracetic acid).

Such stabilizers can take the form of an anionic surfactant or a sequestrant capable of complexing typically di-, tri-, or polyvalent metal cations. Such stabilizer compounds should be in the form of FDA approved non-toxic substances. Anionic surfactants are typically selected from the group of compounds characterized as carboxylate, sulfonate, sulfate, or phosphonate compounds. Carboxylates typically include C$_{9-21}$ alkyl carboxylic acid salts or derivatives thereof including polyalkoxy carboxylates and N-azosarcosanates. Sulfonates generally include alkyl, aryl, or alkyl aryl sulfonates. Sulfates and sulfated products generally include a sulfate group (—SO$_3$M wherein M is typically an alkali metal). Other sulfates include ethoxylated and sulfated alkyl phenols. Chelating agents or sequestrants are compounds containing donor atoms that can combine with metal ions through coordinate bonding to form a sequence structure called a chelated complex or a chelate. There are inorganic and organic chelating agents. Useful inorganic chelating agents primarily comprise polyphosphinate compounds which are relatively inexpensive. Important organic chelating agents includes phosphonic acids, amino and hydroxy carboxylic acids, 1,3-di-ketones, hydroxy carboxylic acids, polyamines, amino alcohols, aromatic heterocyclic bases, phenols, amino phenols, oxime Schiff base and others.

The peracetic acid concentrates of the invention are most effectively produced by combining hydrogen peroxide, a source of acetic acid, and water. Typically, about 50 wt-% of aqueous hydrogen peroxide (50%) can be combined with about 30 wt-% of acetic acid (50%) or acetic anhydride. The balance of the material is commonly made up by deionized or other non-pyrogenic water. The dye or stabilizer can be added to the reaction mixture when combined with a reactant or can be added at some point after the peracetic acid has reached equilibrium through a reaction between acetic acid and hydrogen peroxide. Preferably, the peracetic solutions of the invention are made by combining about 30% of acetic acid (50%), about 50% of aqueous hydrogen peroxide (50% in water). Once the peracetic acid solution has been prepared then the colorant materials are added.

The concentrates of the invention can be diluted using known means with deionized or other acceptable USP sources of water to form the actual use or sanitizing solution. Both the concentrates and the sanitizing or use solutions may have a detectable color due to the colorant of the invention depending upon when the colorant is added. In a particular, preferred embodiment, the colorant materials are added to the peroxy acid comosition upon dilution to a use or make-up solution. A make-up solution is diluted concentrate which can be further diluted or combined with other components to form a use composition.

In the concentrate compositions of the invention, the colorants may be used up to their soubility limits as long as they do not affect the operation of the sterilant and at least up to any limits which may be imposed under federal or state regulations. Generally, the colorants are present in an amount of about 0.001 to 10 wt-%, preferably for reasons of stability and economy, about 0.001 to 1 wt-% and most preferably, about 0.001 to 0.1 wt-%. In the diluted use or sanitizing solutions, the colorants are used at concentrations that range from about 0.001 to 1 wt-%, most preferably for reasons of utility and economy, about 0.001 to 0.01 wt-%.

Finally, the colorants may be added as a solid or liquid. Solid colorants may be powdered, pelletized, tabletted, granulated or formed in any other manner which would allow easy handling and ready dissolution in the peroxy carboxylic acid solution. When the colorant is to be added to the concentrate upon dilution to a make-up or use solution, the colorant is preferably supplied in a premeasured amount. This may be accomplished using premeasured containers of powdered, granulated or liquid materials, or using tablets or pellets sized according to the volume or weight of solution to be colored.

The colored percarboxylic acid solutions of the present invention may be used in any acid sanitizing applications where the presence of the colorant would not be detrimental. Such uses include, for example, peroxy acid CIP (clean in place) sanitizers in the dairy and brewing industries and sanitizers for hospital dialysis units.

CIP sanitizers are use to kill microorganisms in dairy, brewing and other food processing industries. The sanitizer is applied directly to the equipment to clean it without the need for its removal or disassembly. Preferably, the sanitizer is safe for public consumption or it quickly forms such decomposition products. This obviates the need to further clean the sanitizing composition from the process equipment.

Hospital dialysis units are often based on hollow fibers membranes having a microporous structure. Commonly, the hollow fiber membranes are assembled in bundles held within a dialyzer cartridge or shell. The hollow fiber membrane or cartridge containing the membrane is commonly manufactured and stored prior to use in aqueous solutions to protect the fibers from bacterial growth and from losing its transport characteristics. When stored in aqueous solutions, the fiber constituents can provide a growth medium for a variety of microorganisms including bacteria, fungi, etc. Such microorganisms can result in the degradation of the hollow fiber membrane resulting in the membrane being useless for its intended use. Further, the microorganisms can create toxic substances in the cartridge that, if used in dialysis, could result in harm to the patient. Thus, the dialysis units are usually maintained in a sterilizing solution to prevent the growth of harmful microorganisms.

During sanitization, the hollow fiber membranes and hollow fiber membrane containing dialyzer cartridges are held immersed in a dilute peracetic acid sterilant solution for a period of time prior to introduction and use in a dialyzer machine. Thus, for use as a dialysis cartridge sanitizer, the peracetic acid is preferably compatible with the fiber and non-staining. Cartridges can be contained within any suitable container for peracetic acid material after manufacture, during shipment, in storage, at a treatment facility, or just prior to installation in the dialyze machine. Before introduction into the machine, the cartridge is usually flushed with dialyzer fluid in the exterior circuit of the cartridge and, in the membrane interior, with fluid that is physiologically compatible with the blood prior to the initiation of dialysis.

EXAMPLES

The above invention is further illustrated with reference to the following examples which contain a best mode.

EXAMPLE 1

The following Table I contains details regarding the initial preparation of a series of samples that explore the stability of 3-[[4-(phenylamino)phenyl]azo]-benzenesulfonic acid sodium salt dye in various concentrations of hydrogen peroxide and peracetic acid. The samples were made up in 8 ounce glass bottles, equipped with plastic screw caps, and were approximately 200 g.

TABLE I

| | Stability Samples | | |
|---|---|---|---|
| Sample | Initial Peracetic Acid Conc. (wt-%) | Dye Conc. (wt-%) | Color |
| 1 | 4.50 | 0.00 | Clear |
| 2 | 4.50 | 0.01 | Yellow |
| 3 | 0.90 | 0.00 | Clear |
| 4 | 0.90 | 0.01 | Yellow |
| 5 | 0.14 | 0.00 | Clear |
| 6 | 0.14 | 0.01 | Yellow |

The above samples were prepared, and initially those containing dye had strong stable colors. Within 24 hours of preparation, all colors of the dyed samples changed to yellow. The lower concentrations have light but very detectible yellow color.

After five days, the samples were titrated with potassium permangate to determine hydrogen peroxide and sodium thiosulfate to determine peracetic acid. The following Table II sets forth the experimental results.

TABLE II

| | | Titration of Hydrogen Peroxide in Peracetic Acid After Five Days Storage | | | | |
|---|---|---|---|---|---|---|
| Sample No. | Sample Wt. (gm) | Potassium Permangate Vol. (ml) | Sodium Thiosulfate Vol. (ml) | Hydrogen Peroxide Conc. (wt-%) | Peracetic Acid Conc. (wt-%) | Color* |
| 1 | 0.1074 | 13.60 | 11.00 | 21.50 | 3.830 | Clear |
| 2 | 0.1069 | 13.43 | 11.08 | 21.40 | 3.870 | Yellow |
| 3 | 0.5057 | 13.74 | 7.23 | 4.62 | 0.530 | Clear |
| 4 | 0.4755 | 13.57 | 7.00 | 4.68 | 0.540 | Light Yellow |
| 5 | 3.2248 | 12.35 | 8.27 | 0.65 | 0.095 | Clear |
| 6 | 3.2853 | 12.48 | 8.56 | 0.65 | 0.097 | Light Yellow |

*Color seemed largely unchanged since preparation.

An inspection of the columns displaying hydrogen peroxide and peracetic acid concentrations shows that there is no drop off in the concentration of the active materials due to the presence of dye. Some reduction in concentration occurred due to material decomposition that is not dye related.

EXAMPLE 2

A Fresenius F-80 dialyzer cartridge was filled with approximately 150 ml of a dyed peracetic acid solution prepared from Example 1, Sample No. 2 diluted to approximately 0.1 wt-% peracetic acid. The dyed peracetic acid solution was left in contact with the hollow fiber membranes for 24 hours. After 24 hours, the dialyzer cartridge was drained of the dyed peracetic acid solution. The dye did not appear to lose color, the fibers remained white, clear and unchanged.

EXAMPLE 3

Three months after the preparation of the dyed solution set forth in Table I, visual inspection of the samples indicated that the dye remained essentially unchanged in depth and the peracetic acid solutions remained active.

EXAMPLE 4

Various dyes were tested for their color stability in an aqueous solution of hydrogen peroxide and peracetic acid. The results are shown in Tables III and IIIa.

TABLE III

| | Summary of Dyes Tested for their Color Stability In a Peracid Concentrate* | | | | |
|---|---|---|---|---|---|
| Name of Dye | Color at Preparation Time | Color at 48 Hours | Color at 2 weeks | Fiber Staining Capability Polysulfone | Polypropylene |
| Prussian Blue | Dark royal blue | Dark royal blue | Dark royal blue | Yes | Yes |
| Azorubin | Deep crimson red | Cherry red | Light orange | Yes | No |
| Erioglaucine | Very dark green | Bright yellow | Bright yellow | No | No |
| Solvent Blue | Deep turquoise | Light turquoise | Very light blue prepipitates | Yes | Yes |
| Sulforhodamine | Bright pink/red | Light orannge | Very light orange | No | No |
| Naphtol Green B | Olive green | Light yellow | Very light yellow | No | No |
| Solvent Blue 35 | Immiscible | Immiscible | Immiscible | N/T | N/T |
| Fluorescein | Fluorescent yellow | Clear | Clear | N/T | N/T |
| Methylene Blue | Light Blue | Clear | Clear | N/T | N/T |
| Malachite Green | Deep green | Clear | Clear | N/T | N/T |
| Blue Dextran | Light blue | Clear | Clear | N/T | N/T |
| Guinea Green B | Emerald green | Clear | Clear | N/T | N/T |
| Indigo | Immiscible | Immiscible | Immiscible | N/T | N/T |
| Acridine Orange | Gold | Clear | Clear | N/T | N/T |
| Disperse Red 13 | Dark orange (cloudy) | Clear | Clear | N/T | N/T |
| Disperse Yellow 42 | Bright yellow (cloudy) | Bright yellow (cloudy) | Bright yellow (dye precipitates) | N/T | N/T |
| Sudan III | Immiscible | Immiscible | Immiscible | N/T | N/T |
| Safranin O | Translucent red | Very pale pink | Clear | N/T | N/T |
| Crystal Violet | Dark green | Clear | Clear | N/T | N/T |
| Phioxine B | Light orange (not completely soluble) | Light orange (not soluble) | Light orange (not soluble) | N/T | N/T |
| Quinoline Yellow | Clear | Clear | Clear | N/T | N/T |
| Direct Yellow 62 | Clear | Clear | Clear | N/T | N/T |
| Fluorescent Brightener 28 | Clear | Clear | Clear | N/T | N/T |
| Acid Blue 113 | Deep burgundy (not completely soluble) | Solution gold (Dye precipitated) | Immiscible | No | N/T |
| Resolin Violet RL 200 | Deep violet | Deep violet | Immiscible | Yes | N/T |

TABLE III-continued

Summary of Dyes Tested for their Color Stability In a Peracid Concentrate*

| Name of Dye | Color at Preparation Time | Color at 48 Hours | Color at 2 weeks | Fiber Staining Capability | |
|---|---|---|---|---|---|
| | | | | Polysulfone | Polypropylene |
| Red Food Color** | Light Red | Clear | Clear | N/T | N/T |
| Green Food Color** | Light green | Very light green | Very light green | N/T | N/T |

*0.01 wt-% dye
**Exact concentration not known since liquid used.
N/T = Not Tested

TABLE IIIz

Summary of Dyes Tested for their Color Stability In a Peracid Concentrate*

| Name of Dye | Color at Preparation Time | Color at 48 Hours | Color at 2 weeks | Fiber Staining Capability | | |
|---|---|---|---|---|---|---|
| | | | | Poly-sulfone | Cellulose Acetate | Cellulose Tri-Acetate |
| FD & C Yellow #5 | Bright yellow | Bright yellow | Bright yellow | No | No | No |
| FD & C Red #40 | Bright red | Bright red | Red/orange | No | No | No |
| FD & C Red #3 | Bright orange | Bright orange | Light gold | No | No | No |
| FD & C Blue #1 | Dark green | Rusty orange | Rusty orange | No | No | No |

*0.1 wt-% dye

EXAMPLE 5

The following Table IV contains details regarding the stability of two dyes in a hydrogen peroxide/peracetic acid solution. Sample 1 was control (without dye), Sample 2 had 0.01 wt-% N-Ethyl-N-[4-[[4-]ethyl[(3-sulfophenyl)methyl]amino]phenyl](2-sulfophenyl)methylene]-2,5-cyclohexadien-1-ylidene]-3-sulfobenzenemethan-aminium hydroxide inner salt, disodium salt, and Sample 3 is 0.1 wt-% 4,5-dihydro-5-oxo-1-(4-sulfo phenyl)-4-[(4-sulfophenyl)azo]-1H-pyrazole-3-carboxylic acid trisodium salt. The samples were made up in 8 oz. glass bottles, equipped with plastic screw caps, and were approximately 200 g. After the indicated time, the samples were titrated with potassium permanganate to determine hydrogen peroxide and sodium phiosulfate to determine peracetic acid. The following Table IV sets forth the experimental results.

TABLE IV

Stability of FD&C Dyes in Concentrated Peracetic Acid Steriliant Solution*

| | Concentration at 1 Week | | Concentration at 2 Weeks | | Concentration at 3 Weeks | | Concentration at 4 Weeks | |
|---|---|---|---|---|---|---|---|---|
| | $H_2O_2$ | PAA | $H_2O_2$ | PAA | $H_2O_2$ | PAA | $H_2O_2$ | PAA |
| 0.1% FD&C Blue #1 | 19.8% | 3.61% | 19.8% | 3.72% | 19.15% | 3.55% | 19.5% | 3.7% |
| 0.1% FD&C Yellow #5 | 20.1% | 3.56% | 19.7% | 3.69% | 19.5% | 3.6% | 18.9% | 3.54% |
| Control (No Dye) | 19.7% | 3.59% | 19.7% | 3.65% | 19.42% | 3.56% | 19.17% | 3.57% |

*Aqueous solution of 20 wt-% hydrogen peroxide and 4 wt-% peracetic acid.

An inspection of the data shows that there is no drop off in the concentration of the active materials due to the presence of the dye. The numerical values are all within experimental error.

EXAMPLE 6

Three identical aqueous solutions of concentrated peracetic acid (4 wt-%) in hydrogen peroxide (20 wt-%) sterilant were prepared. The first solution was used as a control (Sample 1), the second solution was added to 0.2 g of N-Ethyl-N-[4-[[4-]ethyl[(3-sulfophenyl)methyl]amino]phenyl](2-sulfophenyl)methylene]-2,5-cyclohexadien-1-ylidene]-3-sulfobenzenemethan-aminium hydroxide inner salt, disodium salt to form 200 g of a 0.1 wt-% solution (Sample 2), and the third solution was added to 0.2 g of 4,5-dihydro-5-oxo-1-(4-sulfo phenyl)-4-[(4-sulfophenyl)azo]-1H-pyrazole-3-carboxylic acid trisodium salt to form 200 g of a 0.1 wt-% solution (Sample 3). The three samples were then diluted by adding deionized water to 63 g of each concentrated solution to form 300 g of a solution of 21% of the selected sample in water. The samples were then periodically titrated with potassium permanganate and sodium thiosulfate to determine hydrogen peroxide and peracetic acid concentrations respectively. The following Table V sets forth the experimental results.

TABLE V

| | Sample 1 (Control) | | Sample 2 | | Sample 3 | |
|---|---|---|---|---|---|---|
| | $H_2O_2$ Conc. | PAA Conc. | $H_2O_2$ Conc. | PAA Conc. | $H_2O_2$ Conc. | PAA Conc. |
| Day of Prep. | 4.53% | 0.81% | 4.21% | 0.74% | 4.18% | 0.75% |
| 1 | 4.35% | 0.78% | 4.20% | 0.77% | 4.14% | 0.76% |
| 3 | 4.35% | 0.63% | 4.28% | 0.59% | 4.27% | 0.58% |
| 6 | 4.45% | 0.44% | 4.26% | 0.46% | 4.33% | 0.44% |
| 7 | 4.48% | 0.44% | 4.31% | 0.50% | 4.31% | 0.43% |
| 9 | 4.51% | 0.39% | 4.34% | 0.39% | 4.30% | 0.40% |

A comparison of the data for the control and two test samples indicates that, while there may be some decrease of peroxyacetic acid levels, there is no drop off in the concentration of the active materials due to the presence of the dye. Some reduction in concentration occurred due to material decomposition that is not dye related.

EXAMPLE 7

In a manner similar to that outlined in Example 5, a 0.1 wt-% solution of 3-[[4-(phenyl amino)phenyl]azo]-benzene sulfonic acid dye (basacid yellow 232) was dissolved in an aqueous solution of 20 wt-% hydrogen peroxide and 4 wt-% peracetic acid. A similar container was filled with the above aqueous solution without any dye (Control). The solutions were stored in a dark chamber at room temperature. The hydrogen peroxide and peracetic acid concentrations were monitored. The results are shown below in Table VI.

TABLE VI

| Stability of Basacid Yellow 232 in Concentrated Peracetic Acid Sterilant Solution | | | | | |
|---|---|---|---|---|---|
| Concentration at Preparation | | Concentration at 4 Months | | Concentration at 6 Months | |
| $H_2O_2$ | PAA | $H_2O_2$ | PAA | $H_2O_2$ | PAA |
| Basacid Yellow 20.6% | 3.80% | 18.6% | 3.59% | 17.4% | 3.1% |
| Control 21.5% | 3.83% | 19.0% | 3.53% | 18.0% | 3.20% |

Again, a comparison of the data for the control and two test samples indicates that while there may be some decrease of peroxyacetic acid levels, there is no drop off in the concentration of the active materials due to the presence of the dye. Some reduction in concentration occurred due to material decomposition that is not dye related.

COMPARATIVE TESTING

Other dyes were added to the peracetic sterilant compositions of the invention. The results are shown above in Table III. An inspection of this data shows that numerous dyes are unsuitable for long periods in the oxidizing sanitizing environment, but they may be useful when long term stability is not required. Commonly, our experience shows that the typical dye loses color within 1 to 5 days of the initial sample preparation.

The above description, Examples, and data provide a basis for understanding the invention. However, since many embodiments of the invention can be obtained without departing from the spirit and the scope of the invention, the invention resides in the claims hereinafter appended.

We claim:

1. A stable, colored aqueous peracetic acid solution, having a sanitizing, oxidizing environment, comprising:
   (a) a major proportion of water;
   (b) an effective sanitizing amount of a reaction product containing a percarboxylic acid, the reaction product resulting from a reaction of a source of carboxylic acid and a source of peroxide; and
   (c) a dye which is color-stable in the sanitizing, oxidizing environment for a useful period of time; wherein staining characteristics of the dye are such that polysulfone fibers exposed to the dye in the oxidizing environment of the percarboxylic acid solution remain substantially free of color resulting from exposure to the dye; wherein the dye comprises a compound having a formula selected from the group consisting of:

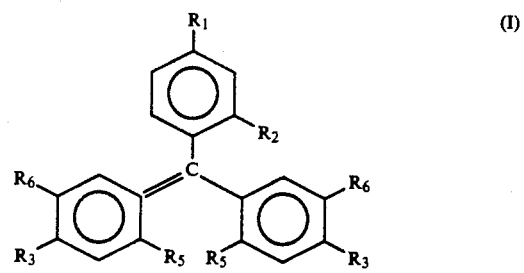

wherein $R_1$ and $R_2$ independently represent —H, —$SO_3M$ wherein M represents $H^+$ or an alkali metal or alkaline earth metal salt; each $R_3$ independently represents —H, —$N(R_4)_2$, or =$N^+(R_4)_2$; $R_4$ represents —H, or $C_{1-4}$ alkyl; each $R_5$ independently represents —H, —$SO_3M$ wherein M represents $H^+$ or an alkali metal or alkaline earth metal salt, or $R_5$ together represent —O—; $R_6$ independently represents —H, or $C_{1-4}$ alkyl;

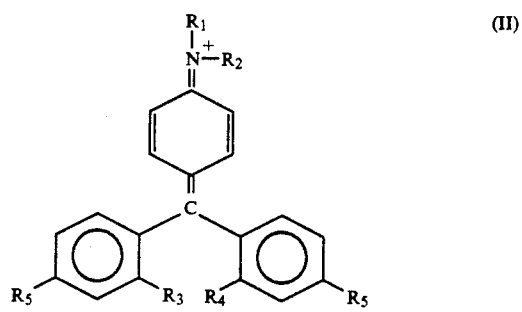

wherein $R_1$ represents —H or $C_{1-4}$ benzyl; $R_3$ and $R_4$ independently represent —H, —$SO_3M$ wherein M represents $H^+$ or an alkali metal or alkaline earth metal salt; and $R_5$ independently represents —H, or —$N(R_6)R_7$ wherein $R_6$ represents —H, $C_{1-4}$ alkyl benzene or —$SO_3M$ substituted $C_{1-4}$ alkyl benzene; and

where Ar and Br are independently

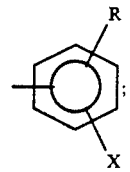

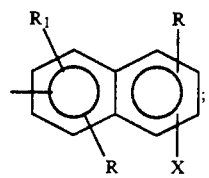

or

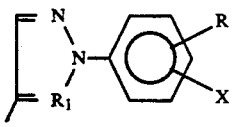

wherein each X represents —H or —SO₃M wherein M represents H⁺ or an alkali metal or alkaline earth metal salt; and R independently represents —H, a $C_{1-12}$ alkyl, a phenyl, a $C_{1-12}$ substituted phenyl, a —NH—$C_{1-12}$ alkyl, a —NH-phenyl, a —NH—$C_{1-12}$ alkyl substituted phenyl, wherein at least one X is not H⁺ and at lest one R is not —H and $R_1$ represents —H or —OH.

2. A stable, colored aqueous peracetic acid solution, having a sanitizing, oxidizing environment, comprising:
  (a) major proportion of water;
  (b) an effective sanitizing amount of a reaction product containing peracetic acid, the reaction product resulting from a reaction of a source of acetic acid and a source of peroxide; and
  (c) an azo dye of the formula:

wherein Ar and Br are independently selected from the group consisting of:

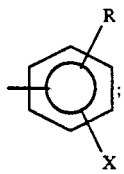

and

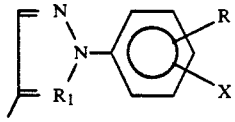

wherein each X represents —H or SO₃M wherein M represents H⁺ or an alkali metal or alkaline earth metal salt; R independently represents —H, a $C_{1-12}$ substituted phenyl, a —NH—$C_{1-12}$ alkyl, a —NH—phenyl, a —NC—$C_{1-12}$ alkyl substituted phenyl, wherein at least one X is not H⁺ and at least one R is not —H; $R_1$ represents —H or —OH; wherein the color of the azo dye is stable in the sanitizing, oxidizing environment for a useful period of time and staining characteristics of the azo dye are such that polysulfone fibers exposed to the dye in the oxidizing environment of the percarboxylic acid solution remain substantially free of color resulting from exposure to the dye.

3. The solution of claim 2 wherein the source of acetic acid comprises acetic acid.

4. The solution of claim 2 wherein the source of acetic acid comprises acetic anhydride.

5. The solution of claim 2 wherein the source of peroxide comprises hydrogen peroxide.

6. The solution of claim 2 wherein the reaction product of subpart (b) is present in the aqueous solution in an amount of about 0.1 to 75 wt-%.

7. The solution of claim 2 wherein for each part of source of acetic acid there is about 0.1 to 20 parts by weight of the source of peroxide, and there is about 0.1 to 35 wt-% of H₂O₂ and about 0.01 to 10 wt-% of peracetic acid.

8. The solution of claim 7 wherein the source of acetic acid comprises acetic acid and the source of peroxide comprises hydrogen peroxide.

9. The solution of claim 2 wherein for each part of source of acetic acid there is about 1 to 2 parts by weight of the source of peroxide, and there is about 20 to 25 wt-% of H₂O₂ and about 3 to 5 wt-% of peracetic acid.

10. A stable, colored aqueous peracetic acid solution having a sanitizing, oxidizing environment, comprising:
  (a) a major proportion of water;
  (b) about 0.1 to 50 wt-% of a reaction product of acetic acid and about 0.5 to 10 parts by weight of hydrogen peroxide per each part of acetic acid; and
  (c) an azo dye of the formula:

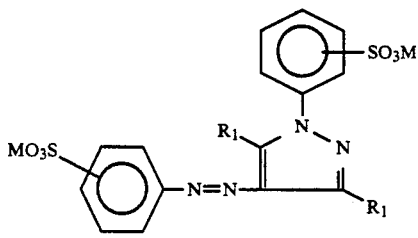

wherein each $R_1$ independently represents a —H, —OH, or COOM and M represents H⁺ or an alkali metal or alkaline earth metal salt; and wherein the color of the azo dye is stable in the sanitizing, oxidizing environment for a useful period of time and staining characteristics of the azo dye are such that polysulfone fibers exposed to the dye in the oxidizing environment of the percarboxylic acid solution remain substantially free of color resulting from exposure to the dye.

11. The solution of claim 10 wherein the reaction product is present at a concentration of from about 0.001 to 0.01 wt-%.

12. The solution of claim 11 wherein for each part of acetic acid there is about 1 to 2 parts of hydrogen peroxide.

13. The solution of claim 10 wherein for each part of source of acetic acid there is about 0.1 to 20 parts by weight of the source of peroxide, and there is about 0.1 to 35 wt-% of H₂O₂ and about 0.01 to 10 wt-% of peracetic acid.

14. The solution of claim 10 wherein for each part of source of acetic acid there is about 1 to 2 parts by weight of the source of peroxide, and there is about 20 to 25 wt-% of H₂O₂ and about 3 to 5 wt-% of peracetic acid.

15. The solution of claim 10 wherein the azo dye comprises 4,5-dihydro-5-oxo-1-(4-sulfo phenyl)-4-[(4-sulfophenyl)azo]-1H-pyrazole-3-carboxylic acid trisodium salt.

16. A preserved hemodialysis membrane cartridge comprising;
  (a) a hemodialysis cartridge comprising a housing having an inlet and an outlet for human blood or blood fraction, and an inlet and an outlet for a hemodialysis solution wherein the inlet and outlet for human blood is operatively connected to the interior of a hollow fiber membrane and the inlet and outlet for the dialyzer fluid is operatively connected to the exterior of the hollow fiber membrane;

(b) an aqueous percarboxylic acid solution within said cartridge having a sanitizing, oxidizing environment, said aqueous percarboxylic acid solution comprising:

(i) a major proportion of water;
(ii) a reaction product containing percarboxylic acid, the reaction product resulting from a reaction of a source of carboxylic acid and a source of peroxide; and
(iii) an azo dye of the formula:

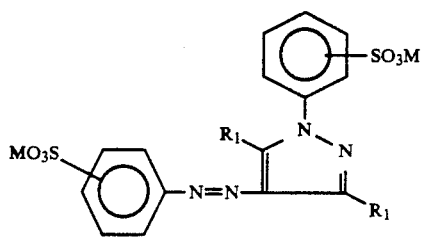

wherein each X represents —H or —$SO_3M$ wherein M represents $H^+$ or an alkali metal or alkaline earth metal salt and R represents a $C_{1-12}$ alkyl, a phenyl, a $C_{1-12}$ substituted phenyl, a —NH—$C_{1-12}$ alkyl, a —NH-phenyl at least on X is not $H^+$ and at least one R is not —H; and wherein the color of the azo dye is stable in a sanitizing, oxidizing environment for a useful period of time and staining characteristics of the azo dye are such that polysulfone fibers exposed to the dye in the oxidizing environment of the percarboxylic acid solution remain substantially free of color resulting from exposure to the dye.

17. The cartridge of claim 16 which the percarboxylic acid comprises a peracetic acid reaction product of a source of acetic acid and a source of peroxide.

18. The cartridge of claim 17 wherein the source of acetic acid comprises acetic acid.

19. The cartridge of claim 17 wherein the source of acetic acid comprises acetic anhydride.

20. The cartridge of claim 17 wherein for each part of source of acetic acid there is about 0.1 to 20 parts by weight of the source of peroxide, and there is about 0.1 to 35 wt-% of $H_2O_2$ and about 0.01 to 10 wt-% of peracetic acid.

21. The cartridge of claim 17 wherein for each part of source of acetic acid there is about 1 to 2 parts by weight of the source of peroxide, and there is about 20 to 25 wt-% of $H_2O_2$ and about 3 to 5 wt-% of peracetic acid.

22. The cartridge of claim 17 wherein for each part of source of acetic acid there is about 0.1 to 20 parts by weight of the source of peroxide.

23. The cartridge of claim 22 wherein the source of acetic acid comprises acetic acid and the source of peroxide comprises hydrogen peroxide.

24. The cartridge of claim 16 wherein the source of peroxide comprises hydrogen peroxide.

25. The cartridge of claim 16 wherein the reaction product of subpart (b) is present in the aqueous solution in an amount of about 0.1 to 75 wt-%.

26. The cartridge of claim 16 wherein the azo dye comprises 4,5-dihydro-5-oxo-1-(4-sulfo phenyl)-4-[(4-sulfophenyl)azo]-1H-pyrazole-3-carboxylic acid trisodium salt.

27. An aqueous peracetic acid solution having a sanitizing, oxidizing environment, comprising:

(a) a major proportion of water;
(b) about 0.1 to 5.0 wt-% of a reaction product containing peracetic acid, the reaction product resulting from a reaction of acetic acid and about 0.1 to 5 parts by weight of hydrogen peroxide per each part of acetic acid wherein there is about 0.05 to 0.5 wt-% of hydrogen peroxide; and
(c) about 0.001 to 1 wt-% of an azo dye of the formula:

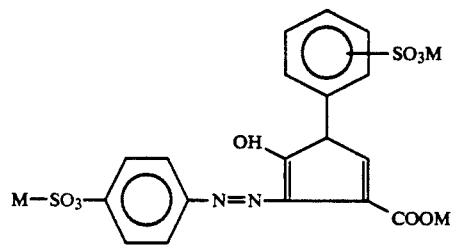

wherein M represents $H^+$ or an alkali metal or alkaline earth metal salt; and wherein the color of the azo dye is stable in the sanitizing, oxidizing environment for a useful period of time; and wherein staining characteristics of the dye are such that polysulfone fibers exposed to the dye in the oxidizing environment of the peracetic acid solution remain substantially free of color resulting from exposure to the dye.

28. An aqueous peracetic acid solution having a sanitizing, oxidizing environment, comprising:

(a) a major proportion of water;
(b) about 3 to 100 wt-% of a reaction product containing peracetic acid, the reaction product resulting from a reaction of acetic acid and about 1 to 2 parts by weight of hydrogen peroxide per each part of acetic acid wherein there is about 3 to 5 wt-% peracetic acid and 0.001 to 0.02 wt-% of hydrogen peroxide; and
(c) about 0.001 to 0.1 wt-% of an azo dye of the formula:

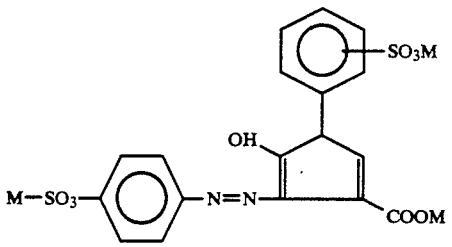

wherein M represents $H^+$ or an alkali metal or alkaline earth metal salt; and wherein the color of the azo dye is stable in the sanitizing, oxidizing environment for a useful period of time; and wherein staining characteristics of the dye are such that polysulfone fibers exposed to the dye in the oxidizing environment of the peracetic acid solution remain substantially free of color resulting from exposure to the dye.

* * * * *